(12) United States Patent
Sun et al.

(10) Patent No.: US 10,293,186 B2
(45) Date of Patent: May 21, 2019

(54) RADIATION THERAPY SYSTEM

(71) Applicant: SOOCHOW UNIVERSITY, Suzhou (CN)

(72) Inventors: Lining Sun, Suzhou (CN); Fengfeng Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 252 days.

(21) Appl. No.: 15/519,425

(22) PCT Filed: Dec. 8, 2014

(86) PCT No.: PCT/CN2014/093215
§ 371 (c)(1),
(2) Date: May 10, 2017

(87) PCT Pub. No.: WO2016/061877
PCT Pub. Date: Apr. 28, 2016

(65) Prior Publication Data
US 2017/0239496 A1 Aug. 24, 2017

(30) Foreign Application Priority Data

Oct. 20, 2014 (CN) .......................... 2014 1 0557823

(51) Int. Cl.
*A61N 5/10* (2006.01)
(52) U.S. Cl.
CPC ......... *A61N 5/1081* (2013.01); *A61N 5/1049* (2013.01); *A61N 5/1069* (2013.01); *A61N 2005/1061* (2013.01)
(58) Field of Classification Search
CPC .......... A61N 2005/1061; A61N 5/1049; A61N 5/1081; A61N 5/1069
See application file for complete search history.

(56) References Cited

U.S. PATENT DOCUMENTS

2011/0301449 A1* 12/2011 Maurer, Jr. ............ A61B 6/032
600/411
2014/0139215 A1* 5/2014 Gregerson ............... A61B 6/04
324/309
(Continued)

FOREIGN PATENT DOCUMENTS

CN 1537656 A 11/2004
CN 101244317 A 8/2008
(Continued)

*Primary Examiner* — Chih-Cheng Kao
(74) *Attorney, Agent, or Firm* — SZDC Law P.C.

(57) ABSTRACT

The invention relates to radiation therapy system. The system includes a five-degree-of-freedom O-shaped arm radiation therapy device and a six-degree-of-freedom parallel radiation therapy bed. The five-degree-of-freedom O-shaped arm radiation therapy device includes an O-shaped arm movement mechanism, a linear accelerator device, a radiation dose detection device and a double-X-ray machine image positioning mechanism. The O-shaped arm movement mechanism includes an O-shaped arm, an accelerator displacement device, a rotational displacement device, a turning displacement device, a horizontal transverse displacement device, and a horizontal longitudinal displacement device. The double-X-ray machine image positioning mechanism includes an X-ray transmitter and receiver. The six-degree-of-freedom parallel radiation includes a base assembly, a connecting rod assembly and a bed plate assembly. The radiation therapy system of the invention achieves five-degree-of-freedom control of a radiation therapy process with high control accuracy and stability, and has flexible spatial positions and high positioning accuracy of the radiation therapy bed.

10 Claims, 9 Drawing Sheets

(56) References Cited

U.S. PATENT DOCUMENTS

2015/0320376 A1* 11/2015 Oishi .................. A61B 6/4405
                                                              378/199
2017/0189719 A1*  7/2017 Liu ..................... A61B 6/0457

FOREIGN PATENT DOCUMENTS

| CN | 102019041 A   |   | 4/2011  |
|----|---------------|---|---------|
| CN | 103071241 A   |   | 5/2013  |
| CN | 103143124 A   |   | 6/2013  |
| CN | 203280909 U   |   | 11/2013 |
| CN | 104307114 A   |   | 1/2015  |
| CN | 204121623 U   |   | 1/2015  |
| CN | 204170301 U   |   | 2/2015  |
| CN | 204219617 U   | * | 3/2015  |

* cited by examiner

RADIATION THERAPY SYSTEM

The present application is the national phase application of International Application No. PCT/CN2014/093215, filed on Dec. 8, 2014, which claims the priority from China Patent application Ser. No. 201410557823.4, filed on Oct. 20, 2014, which is incorporated by reference for all purposes as if fully set forth herein.

FIELD OF THE INVENTION

The present invention relates to a radiation therapy medical apparatus, and particularly to a radiation therapy system.

DESCRIPTION OF THE RELATED ART

Tumors are one of principal diseases harmful to human health. Currently there are three main means for treating tumors: surgery, radiation and drug therapy, where destroying diseased tissues by use of radiation is a widely used method in radiation medicine, and the World Health Organization reports that 45% of tumors can be cured, where tumors that can be cured by radiation therapy reaches 18%. For this purpose, apparatuses using high energy electromagnetic radiation (X-radiation, gamma radiation) or particle radiation (electrons, protons, carbon ions) are utilized. During the radiation therapy, it is required to accurately position a patient to ensure that a body area to be irradiated, particularly tumors to be irradiated receive a sufficiently high radiation dose while health tissues of the patient are damaged as less as possible. This is generally achieved by an X-ray imaging method using radiation in the kilovolt (kV) energy range, particularly by computed tomography, and then the radiation used in the radiation therapy is typically in the megavolt (MV) energy range.

The China Patent Application No. 200710005399.2 discloses a radiation therapy system, including a turning drive unit, an O ring, a movement gantry, a head swing device, and an irradiation device. The irradiation device irradiates a therapeutic radioactive ray under the control of a radiation therapy apparatus controller, and the therapeutic radioactive ray can irradiate toward the isocenter from any direction through movement and rotation. The turning drive unit supports the O ring on a base such that the O ring is rotatable around a rotation axis, and the radiation therapy apparatus further includes a movement drive unit, and the movement drive unit rotates the movement gantry around a rotation axis under the control of the radiation therapy apparatus controller. However, such a radiation therapy system has more controllable degrees of freedom during the radiation therapy, and the mass of the O ring is usually larger such that it is difficult for the turning drive unit for supporting the O ring to accurately control the rotation of the O ring, and further, the rotation of the movement gantry will result in uneven mass distribution at left and right sides of the O ring. Therefore, it is difficult to ensure the control accuracy effectively. The China Patent Application No. 201310115139.6 discloses a robotic noninvasive radiation therapy system, where a six-degree-of-freedom G-shaped arm real-time image system is formed by successively connecting a G-shaped arm, a G-shaped arm slide rail, a G-shaped arm rotation shaft, a G-shaped arm pitch shaft, and a G-shaped arm slide base; an X-ray source and an X-ray dynamic flat panel detector are formed into one group, and two groups of X-ray sources and X-ray dynamic flat panel detectors are correspondingly mounted on the G-shaped arm; the G-shaped arm slide base is mounted in a rail, and the rail is mounted on a ceiling rail on the ceiling or the ground of the therapy room; the G-shaped arm may move up and down, the G-shaped arm slide rail may guide two groups of X-ray sources and X-ray dynamic flat panel detectors to move by more than 90°, and the G-shaped arm may rotate around the G-shaped arm rotation shaft by ±90° and swing around the G-shaped arm pitch shaft by ±15°. However, in such a radiation therapy system, the mass of the G-shaped arm real-time image system is usually larger and mounted on the ceiling, such that not only the ceiling is required to have high supporting capacity, but also mounting and removal are relatively inconvenient, and further, the upper support mode results in that a greater degree of shaking of the G-shaped arm easily occurs during the rotation, thereby influencing accuracy of the radiation therapy.

The existing radiation therapy systems are, as described above, usually designed only for an irradiation device such that the irradiation device has the feature of multi-degree-of-freedom movement, while a radiation therapy bed matching with a radiation therapy head is usually fixed or only has the function of one-way movement. The China Patent Publication No. CN202876109U discloses such a therapy bed of a radiation therapy system, including a longitudinal slide bed plate, a longitudinal slide guide, a longitudinal slide block, a transverse slide bed plate, a detection probe, a lifting bed plate, and a base, where the longitudinal slide bed plate is located above the longitudinal slide block, the longitudinal slide guide is slidably connected with the longitudinal slide block, the transverse slide bed plate is located below the longitudinal slide guide, the detection probe is fixed at one end of the transverse slide bed plate, the lifting bed plate is located below the transverse slide bed plate, and the base is located below the lifting bed plate. However, the existing radiation therapy bed has several problems in use: 1) a clinically conventional radiotherapy device, such as an X-ray machine, a cobalt-60 therapy machine, a betatron, an electron linear accelerator and an cyclotron, has limited radiation field, with the maximum radiation field of usually 40 cm, and in fact, diseased regions of some patients that require radiotherapy are elongated with a length of up to 60 cm (for example, spinal cord cancer), and although diseased regions beyond the maximum radiation field of the device can be treated segment by segment using a radiation field segmentation method, phenomenons that radiation field regions are overlapped or some diseased regions may not be irradiated will occur inevitably, this will influence the therapeutic effects and reduces the efficiency, and it is difficult to achieve adjustment of the existing radiation therapy bed over a large range of displacement to meet the requirement of the radiation field; and 2) positions where tumors are located are randomly distributed and very likely blocked by other organs, it is required to adjust positions of the therapy bed to cooperate with the therapy head for the optimal therapeutic effects, thereby avoiding damage to health tissues, and it is difficult to achieve adjustment of the existing radiation therapy bed within a large range of angles and positions.

SUMMARY OF THE INVENTION

The technical problem to be solved by the present invention is to provide a radiation therapy system, and the system can achieve five-degree-of-freedom control of a radiation therapy process with high control accuracy and stability, and has flexible spatial positions and high positioning accuracy of a radiation therapy bed.

For the above purpose, one object of the invention is to provide a radiation therapy system, including a five-degree-of-freedom O-shaped arm radiation therapy device and a six-degree-of-freedom parallel radiation therapy bed.

The five-degree-of-freedom O-shaped arm radiation therapy device includes an O-shaped arm movement mechanism, a linear accelerator device, a radiation dose detection device, and a double-X-ray machine image positioning mechanism. The O-shaped arm movement mechanism includes an O-shaped arm, an accelerator displacement device, a rotational displacement device, a turning displacement device, a horizontal transverse displacement device, and a horizontal longitudinal displacement device. The horizontal longitudinal displacement device includes a first slide rail and a first slide base disposed at both sides of the O-shaped arm, and a first power unit configured to drive the first slide base to relatively slide on the first slide rail, there are two sets of the first slide rails and the first slide bases. The horizontal transverse displacement device includes a second slide rail and a second slide base disposed on the first slide base, and a second power unit configured to drive the second slide base to relatively slide on the second slide rail, there are two sets of the second slide rails and the second slide bases, and the slide directions of the second slide bases and the first slide bases are vertical to each other. The turning displacement device includes a third power unit disposed on the second slide base for turning the rotational displacement device, a turning plane of the rotational displacement device is vertical to a slide direction of the second slide base. The rotational displacement device includes a turning seat disposed at an output end of the third power unit and a fourth power unit, the O-shaped arm is disposed between two sets of turning seats, the fourth power unit is used for driving the O-shaped arm to relatively displace on the turning seats. The linear accelerator device is mounted on the O-shaped arm by the accelerator displacement device, and the accelerator displacement device is configured to drive the linear accelerator device to displace relatively towards a central position of the O-shaped arm. The radiation dose detection device is disposed on the O-shaped arm at a side opposite to the linear accelerator device. The double-X-ray machine image positioning mechanism includes a X-ray transmitter disposed on the O-shaped arm and a X-ray receiver disposed on the O-shaped arm at a side opposite to the X-ray transmitter, two sets of the X-ray transmitters and the X-ray receivers are provided.

The six-degree-of-freedom parallel radiation therapy bed includes a base assembly, a connecting rod assembly and a bed plate assembly. The base assembly includes a base, a plurality of sliding rails disposed on the base side by side, and a power unit fixed to the base. The connecting rod assembly includes a sliding base and a connecting rod, the sliding base is driven by the power unit to relatively slide on the sliding rails, and a bottom end of the connecting rod is rotatably connected with the sliding base. The bed plate assembly includes a main bed plate, and a top end of the connecting rod is rotatably connected with the main bed plate.

Preferably, a plurality of annular slide grooves are disposed on a side surface of the O-shaped arm, limiting plates are fixed at both sides of front and rear ends of the turning seat, and slide blocks engaged and relatively sliding in the slide grooves are disposed at the inner side of the limiting plates.

Preferably, the first power unit includes a first servo motor, a first lead screw and a first lead screw sleeve, wherein the first lead screw is disposed at an output end of the first servo motor and mutually parallel to the first slide rail, the first lead screw sleeve is fixed at the bottom of the first slide base and relatively rotatable on the first lead screw.

Preferably, the second power unit includes a second servo motor, a second lead screw and a second lead screw sleeve, wherein the second lead screw is disposed at an output end of the second servo motor and mutually parallel to the second slide rail, the second lead screw sleeve is fixed at the bottom of the second slide base and relatively rotatable on the second lead screw.

Preferably, the third power unit includes a third servo motor fixed to the second slide base, and the turning seat is fixed at an output end of the third servo motor.

Preferably, the fourth power unit includes a fourth servo motor fixed to the turning seat and a driving gear disposed at an output end of the fourth servo motor, wherein a synchronous belt is disposed on the outer side surface of the O-shaped arm, and the fourth servo motor drives relative displacement of the O-shaped arm on the turning seat through interaction of the driving gear and the synchronous belt.

Preferably, the accelerator displacement device includes a base plate fixed to the O-shaped arm, a fifth servo motor fixed to the base plate, a plurality of third lead screws vertically fixed to the bottom of the base plate, and a plurality of third lead screw sleeves fixed to the linear accelerator device and relatively rotatable on the third lead screws.

Preferably, there are six sliding rails, wherein three sliding rails are parallelly disposed on the top surface of the front side of the base and the other three sliding rails are parallelly disposed on the top surface of the rear side of the base. There are six connecting rod assemblies, and the sliding bases of the six connecting rod assemblies relatively slide on the respective sliding rails.

Preferably, the base assembly further includes bearing supports disposed on the top surfaces of the front and rear sides of the base and lead screws disposed parallel to the sliding rails, wherein the power unit is disposed at the middle part of the top surface of the base and located between ends of the sliding rails, one end of the lead screw is disposed on the bearing support by the bearing, the other end of the lead screw is in driving connection with the power unit. A nut sleeve is disposed at the bottom of the sliding base, and the nut sleeve is rotatable relative to the lead screw.

Preferably, the sliding base is rotatably connected to the bottom of the connecting rod by a first cross shaft, and a hooke joint at the bottom of the main bed plate is rotatably connected to the top of the connecting rod by a second cross shaft.

Specifically, bearings are provided respectively between the first cross shaft and the bottom of the connecting rod, between the first cross shaft and the sliding base, between the second cross shaft and the top of the connecting rod, and between the second cross shaft and the hooke joint at the bottom of the main bed plate.

Preferably, the connecting rod includes an upper connecting rod and a lower connecting rod, a thrust bearing is disposed between a top end of the lower connecting rod and a bottom end of the upper connecting rod, and an end cap is further disposed on a bottom end of the lower connecting rod for limiting a relative position of the upper connecting rod and the lower connecting rod, and a copper sleeve cooperating with the bottom of the upper connecting rod is further disposed on the outer side of the top end of the lower connecting rod.

Preferably, the bed plate assembly further includes a middle bed plate, the middle bed plate is fixedly connected with the main bed plate, the main bed plate is a metal main bed plate, and the middle bed plate is a carbon fiber middle bed plate.

Preferably, the bed plate assembly further includes an additional bed plate, and the additional bed plate is fixed at an end of the middle bed plate by a suspension fixture.

By means of the above technical solutions, the present invention at least has the following advantages: in the five-degree-of-freedom O-shaped arm radiation therapy device, the first power unit drives the O-shaped arm to displace along the horizontal longitudinal direction, the second power unit drives the O-shaped arm to displace along the horizontal transverse direction, the third power unit drives the O-shaped arm to achieve turning movement, the fourth power unit drives the O-shaped arm to rotate along the central position, and the accelerator displacement device drives the linear accelerator device to relatively move towards the central position of the O-shaped arm, and in this way, a omni-directional and multi-angle radiation therapy process, high control accuracy and a high degree of stability can be achieved through five-degree-of-freedom adjustment. Furthermore, the double-X-ray machine image positioning mechanism operates by an X-ray imaging method using radiation in the kilovolt (kV) energy range, and radiation used by the linear accelerator device and the radiation dose detection device in the radiation therapy is in the megavolt (MV) energy range. In addition, the six-degree-of-freedom parallel radiation therapy bed overcomes the defects of the existing radiation therapy beds, such as inflexible spatial positions, low positioning accuracy and poor bearing capacity, and the radiation therapy system of the present invention has advantages including flexible spatial positions, high positioning accuracy and strong bearing capacity and can meet the requirements of accurate radiation therapy.

DETAILED DESCRIPTION OF THE PREFERRED EMBODIMENTS

Figure 1:
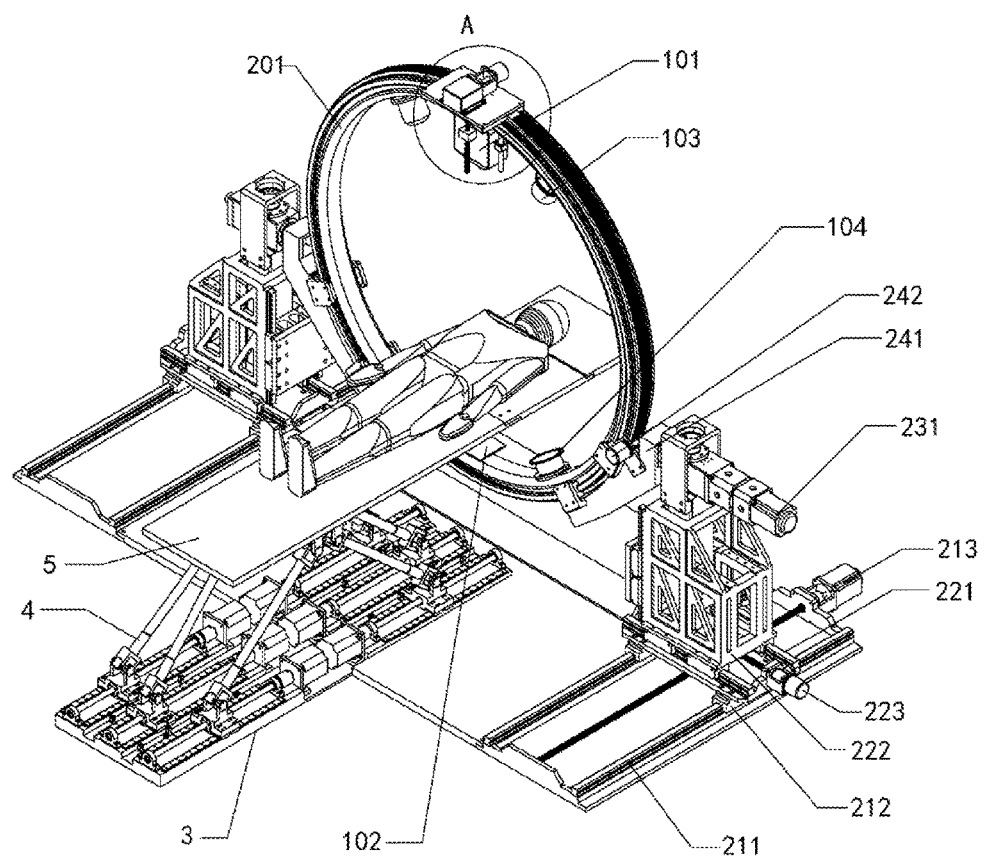
FIG. 1 is a front view of a radiation therapy system of the present invention.

The invention will be further illustrated in more detail with reference to the accompanying drawings and embodiments. It is noted that, the following embodiments only are intended for purposes of illustration, but are not intended to limit the scope of the present invention.

In the description of the present invention, it is to be understood that orientation or positional relations indicated by terms "center", "longitudinal", "transverse", "length", "width", "thickness", "up", "down", "front", "rear", "left", "right", "vertical", "horizontal", "top", "bottom", "inner", "outer", "clockwise", "counter-clockwise" and the like are based on those shown in the accompanying drawings, and they are only intended to facilitate and simplify the description of the present invention, rather than indicating or implying that a device or element indicated by the terms must have a particular orientation, or must be configured and operated at a particular orientation, and thus it should not be construed as limiting the present invention.

In addition, terms "first" and "second" are only used for the purpose of description and should not be construed as indicating or implying relative importance or implicitly indicating the number of the indicated technical feature. Thereby, features defined by terms "first" and "second" may expressly or implicitly include one or more features. In the description of the present invention, unless explicitly and specifically defined otherwise, the meaning of "a plurality of" is two or more.

In the description of the present invention, unless explicitly specified and defined otherwise, terms "mount", "connect", "connection", "fix" and the like should be interpreted in a broad sense, and may be, for example, a fixed connection, detachable connection or integral connection; may also be a mechanical connection or electrical connection; may be a direct connection or indirect connection via an intermediate medium; may also be communication between interiors of two elements or an interaction relationship between two elements. Those of ordinary skill in the art may understand specific meanings of the above-mentioned terms in the present invention according to specific situations.

In the present invention, unless explicitly specified and defined otherwise, a first feature being "above" or "below" a second feature may mean that the first feature is in direct contact with the second feature, and may also mean that the first feature is in non-direct contact with the second feature via another feature therebetween. Further, the first feature being "over", "above" or "on the top of" the second feature may mean that the first feature is directly above and obliquely above the second feature, or may merely indicate that the horizontal height of the first feature is higher than that of the second feature. The first feature being "under", "below" or "underneath" the second feature may mean that the first feature is directly below and obliquely below the second feature, or may merely indicate that the horizontal height of the first feature is lower than that of the second feature.

Figure 2:
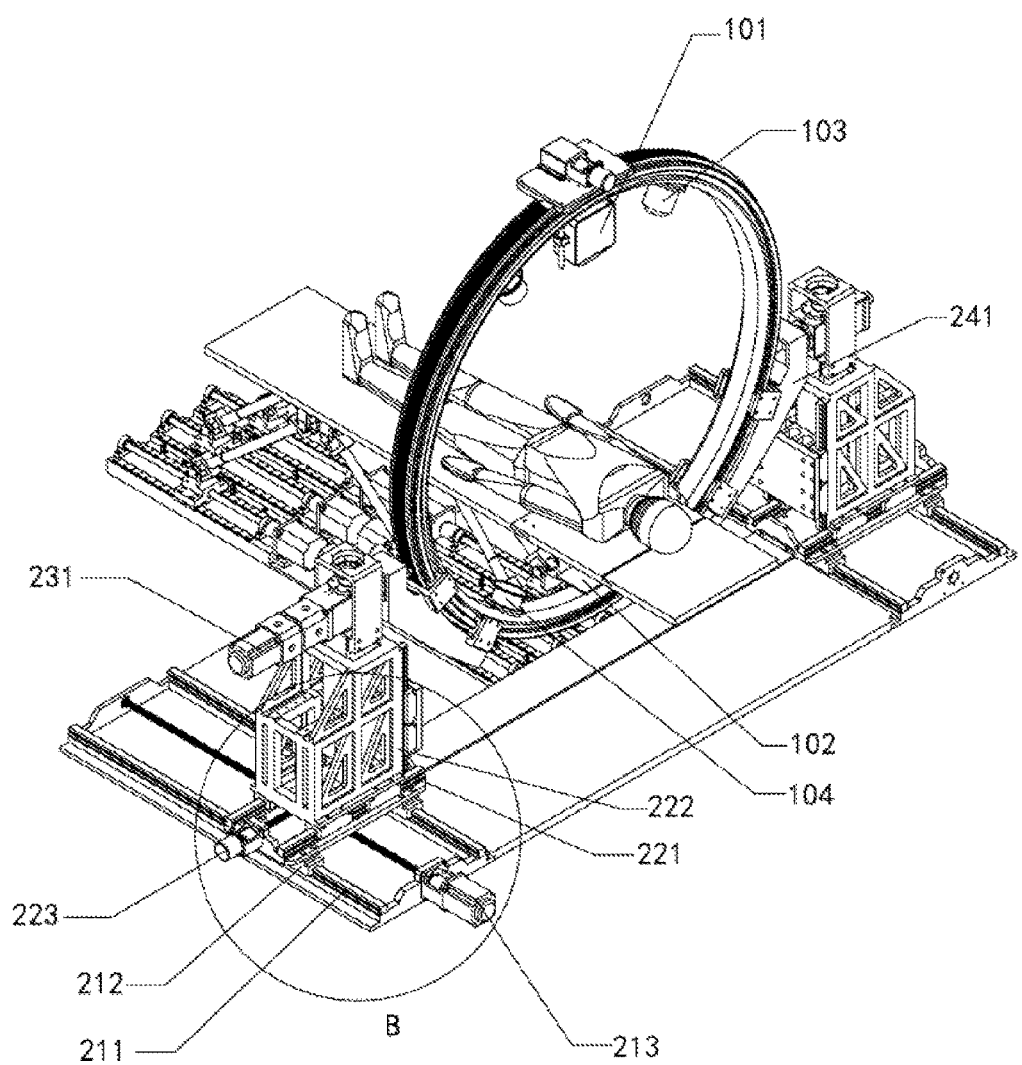
FIG. 2 is a rear view of the radiation therapy system of the present invention.
Figure 3:
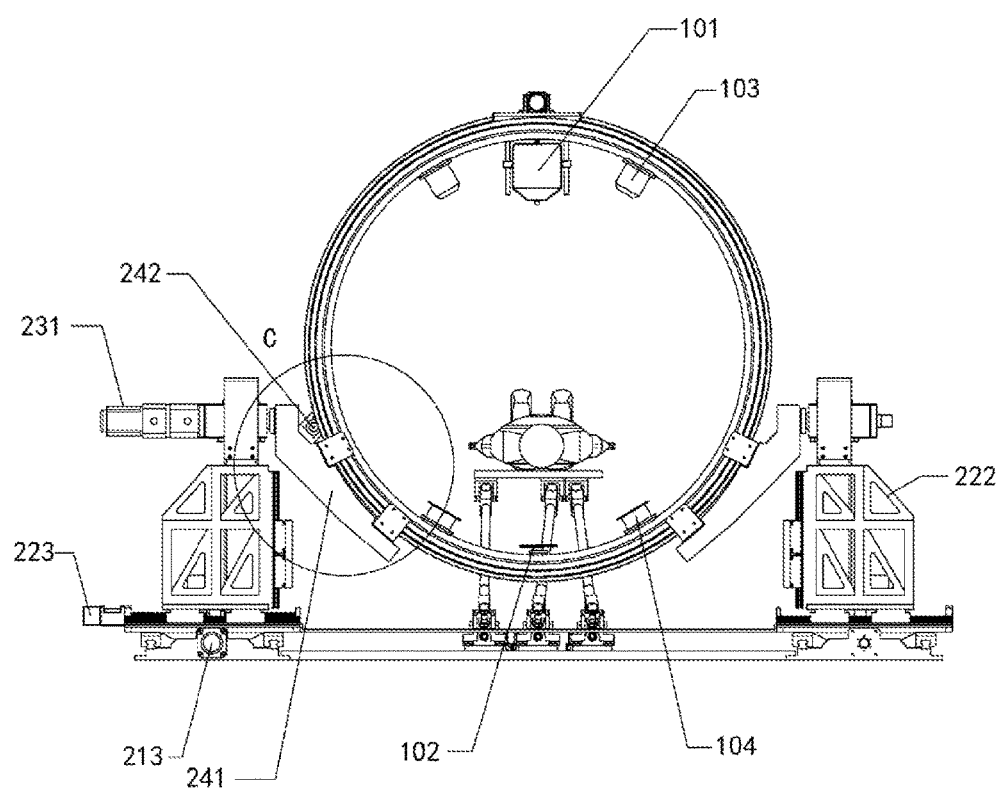
FIG. 3 is a side view of the radiation therapy system of the present invention.
Figure 4:
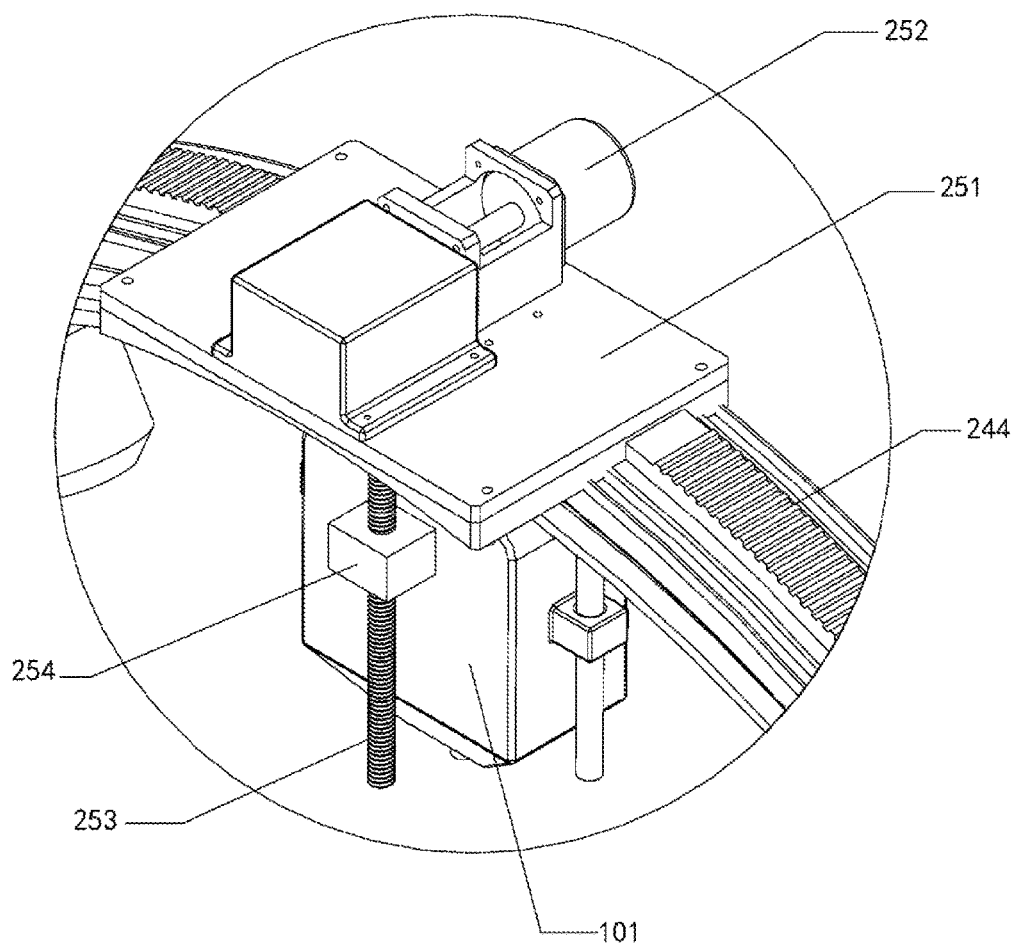
FIG. 4 is a partial enlarged view of portion A in FIG. 1.
Figure 5:
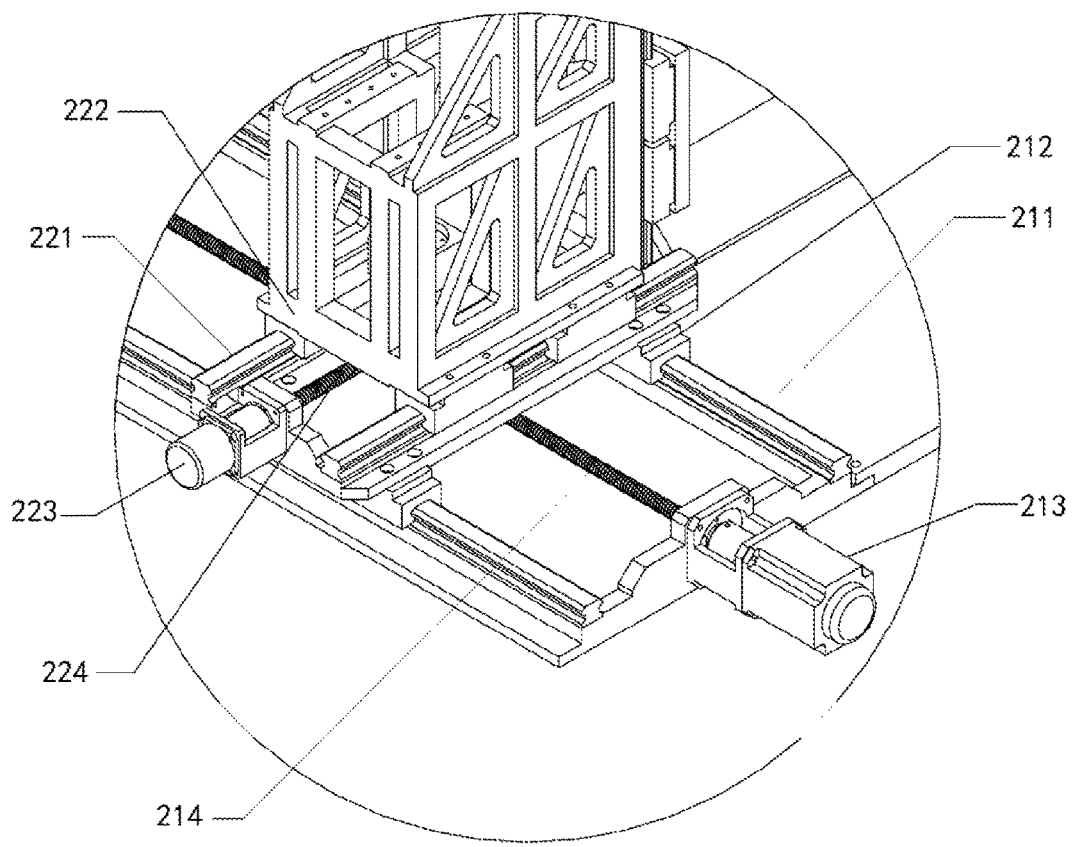
FIG. 5 is a partial enlarged view of portion B in FIG. 2.
Figure 6:
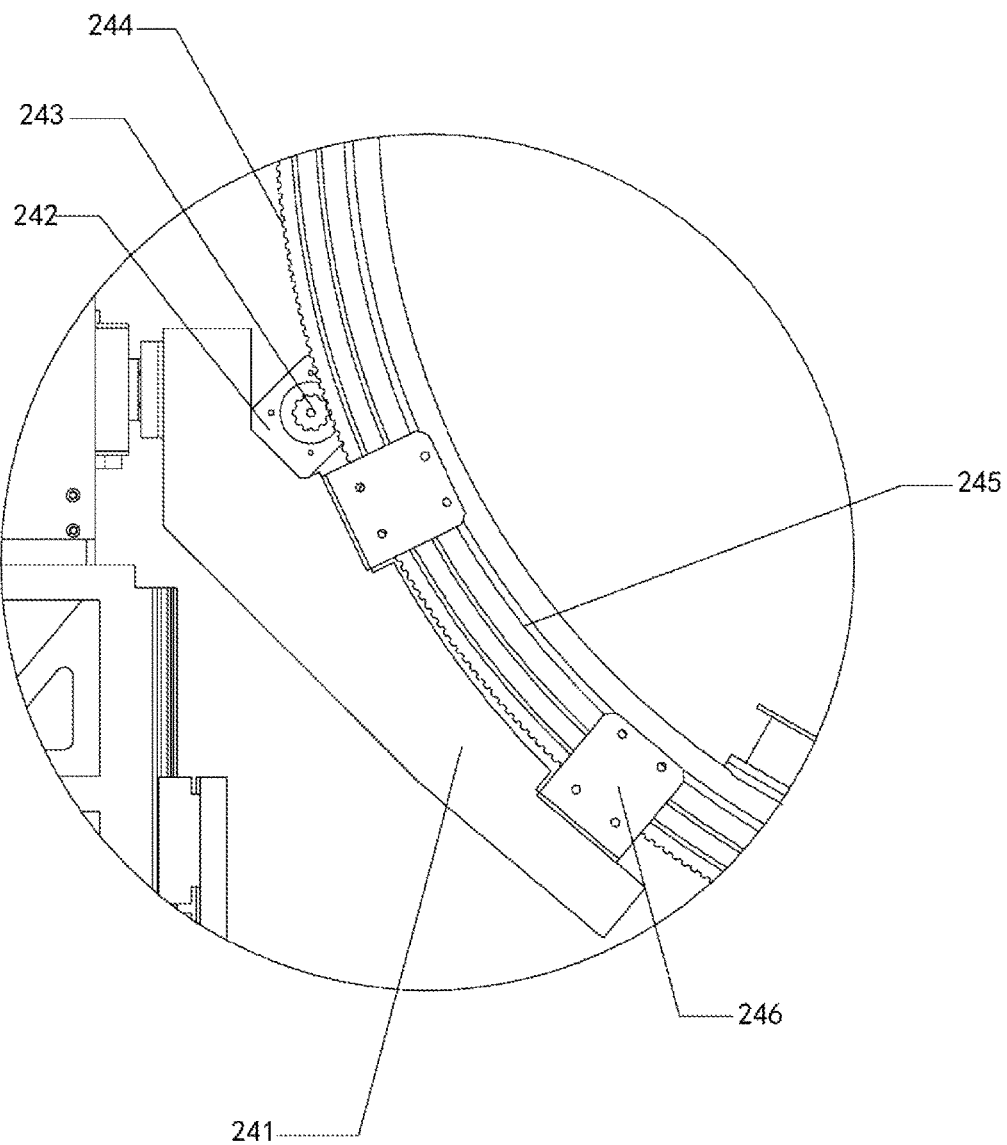
FIG. 6 is a partial enlarged view of portion C in FIG. 3.

Referring to FIGS. 1 to 6, a radiation therapy system of the present invention includes a five-degree-of-freedom O-shaped arm radiation therapy device and a six-degree-of-freedom parallel radiation therapy bed. The five-degree-of-freedom O-shaped arm radiation therapy device includes an O-shaped arm movement mechanism, a linear accelerator device 101, a radiation dose detection device 102, and a double-X-ray machine image positioning mechanism. The O-shaped arm movement mechanism includes an O-shaped arm 201, an accelerator displacement device, a rotational displacement device, a turning displacement device, a horizontal transverse displacement device, and a horizontal longitudinal displacement device.

The horizontal longitudinal displacement device includes a first slide rail 211 and a first slide base 212 disposed at both sides of the O-shaped arm, and a first power unit 213 for driving the first slide base 212 to relatively slide on the first slide rail 211, there are two sets of the first slide rails 211 and the first slide bases 212. There are multiple implementations of the first power unit, for example, 1) an implementation of adopting a hydraulic cylinder to push, where the first power unit is a hydraulic cylinder, the first slide base is disposed at the output end of the hydraulic cylinder, and the first slide base is pushed by the hydraulic cylinder to relatively slide; 2) an implementation of adopting teeth engagement, where the first power unit is a motor, a gear is disposed at the output end of the motor, teeth cooperating with the gear are disposed on the first slide base, and the relative sliding of the first slide base is driven by rotation of the gear; and 3) an implementation of adopting a lead screw, where the first power unit includes a first servo motor, a first lead screw 214 and a first lead screw sleeve (not shown), the first lead screw 214 is disposed at the output end of the first servo motor and parallel to the first slide rail 211, the first lead screw sleeve is fixed at the bottom of the first slide base 212, and the first lead screw sleeve relatively rotates on the first lead screw 214. The foregoing description is only preferred embodiments of the first power unit and not intended to limit the present invention, and it should be noted that, all the first power units which are capable of driving the first slide base to relatively slide on the first slide rail should fall within the scope of protection of the present invention. In addition, since the above-mentioned function can be achieved by disposing the first power unit for the horizontal longitudinal displacement device at either side of the O-shaped arm, the first power unit is provided as one or two groups.

The horizontal transverse displacement device includes a second slide rail 221 and a second slide base 222 disposed on the first slide base 212, and a second power unit 223 for driving the second slide base 222 to relatively slide on the second slide rail 221, there are two sets of the second slide rails 221 and the second slide bases 222, and the slide directions of the second slide base 222 and the first slide base 212 are vertical to each other. There are multiple implementations of the second power unit, for example, 1) an implementation of adopting a hydraulic cylinder to push, where the second power unit is a hydraulic cylinder, the second slide base is disposed at the output end of the hydraulic cylinder, and the second slide base is pushed by the hydraulic cylinder to relatively slide; 2) an implementation of adopting teeth engagement, where the second power unit is a motor, a gear is disposed at the output end of the motor, teeth cooperating with the gear are disposed on the second slide base, and the relative sliding of the second slide base is driven by rotation of the gear; and 3) an implementation of adopting a lead screw, where the second power unit includes a second servo motor, a second lead screw 224 and a second lead screw sleeve (not shown), the second lead screw 224 is disposed at the output end of the second servo motor and parallel to the second slide rail 221, the second lead screw sleeve is fixed at the bottom of the second slide base 222, and the second lead screw sleeve relatively rotates on the second lead screw 224. The foregoing description is only preferred embodiments of the second power unit and not intended to limit the present invention, and it should be noted that, all the second power units which are capable of driving the second slide base to relatively slide on the second slide rail should fall within the scope of protection of the present invention. In addition, since the above-mentioned function can be achieved by disposing the second power unit for the horizontal transverse displacement device at either side of the O-shaped arm, the second power unit is provided as one or two groups.

The turning displacement device includes a third power unit 231 disposed on the second slide base 222 for turning the rotational displacement device, the turning plane of the rotational displacement device is vertical to the slide direction of the second slide base 222. There are multiple implementations of the turning displacement device, for example, by means of control of gear engagement, that is, a driven gear is connected on the rotational displacement device and a driving gear is disposed at the output end of the third power unit; in a relatively simple implementation, by means of control of motor rotation, that is, the third power unit includes a third servo motor fixed to the second slide base and a turning seat is fixed at the output end of the third servo motor. The foregoing description is only the preferred embodiments of the turning displacement device and not intended to limit the present invention, and it should be noted that, all the turning displacement devices which are capable of driving the rotational displacement device to turn should fall within the scope of protection of the present invention. In addition, since the above-mentioned function can be achieved by disposing the third power unit for the turning displacement device at either side of the O-shaped arm, the third power unit is provided as one or two groups.

The rotational displacement device includes a turning seat 241 arranged at the output end of the third power unit 231 and a fourth power unit 242, the O-shaped arm 201 is disposed between two turning seats 241, the fourth power unit 242 is used for driving relative displacement of the O-shaped arm 201 on the turning seats 241. The rotational displacement device can rotate and drive the O-shaped arm by means of multiple implementations, where a relatively simple and stable implementation is as follows: the fourth power unit includes a fourth servo motor fixed to the turning seat 241 and a driving gear 243 disposed at the output end of the fourth servo motor, a synchronous belt 244 is disposed on the outer side surface of the O-shaped arm 201, and the fourth servo motor drives the relative displacement of the O-shaped arm 201 on the turning seats 241 by means of the interaction of the driving gear 243 with the synchronous belt 244. The foregoing description is only the preferred embodiment of the turning displacement device and not intended to limit the present invention, and it should be noted that, all the rotational displacement devices which are capable of driving the O-shaped arm to rotate should fall within the scope of protection of the present invention. In order to effectively stabilize the sliding of the O-shaped arm 201 on the turning seats 241 for accurate control, in the five-degree-of-freedom O-shaped arm radiation therapy device of the present invention, a plurality of annular slide grooves 245 are opened on the side surfaces of the O-shaped arm 201, limiting plates 246 are fixed at both sides of front and rear ends of the turning seats 241, and slide blocks that are engaged and relatively slide in the slide grooves are disposed at the inner side of the limiting plates 246. In addition, since the above-mentioned function can be achieved by disposing the fourth power unit for the rotational displacement device at either side of the O-shaped arm, the fourth power unit is provided as one or two groups.

The linear accelerator device 101 is mounted on the O-shaped arm 201 by the accelerator displacement device, the accelerator displacement device is used to drive relative displacement of the linear accelerator device 101 towards the central position of the O-shaped arm 201, and the radiation dose detection device 102 is disposed on the O-shaped arm 201 at a side opposite to the linear accelerator device 101. The double-X-ray machine image positioning mechanism includes X-ray transmitters 103 disposed on the O-shaped arm 201 and X-ray receivers 104 disposed on the O-shaped arm 201 at a side opposite to the X-ray transmitters 103, and there are two sets of the X-ray transmitters 103 and the X-ray receivers 104. There are multiple implementations of the accelerator displacement device, where a relatively simple and stable implementation is as follows: the accelerator displacement device includes a base plate 251 fixed on the O-shaped arm, a fifth servo motor 252 fixed on the base plate, a plurality of third lead screws 253 vertically fixed to the bottom of the base plate, and a plurality of third lead screw sleeves 254 fixed on the linear accelerator device, the third lead screw sleeves 254 relatively rotate on the third lead screws 253. The foregoing description is only the preferred embodiment of the accelerator displacement device and not intended to limit the present invention, and it should be noted that, all the accelerator displacement devices which are capable of driving the relative displacement of the linear accelerator device should fall within the scope of protection of the present invention.

Figure 7:
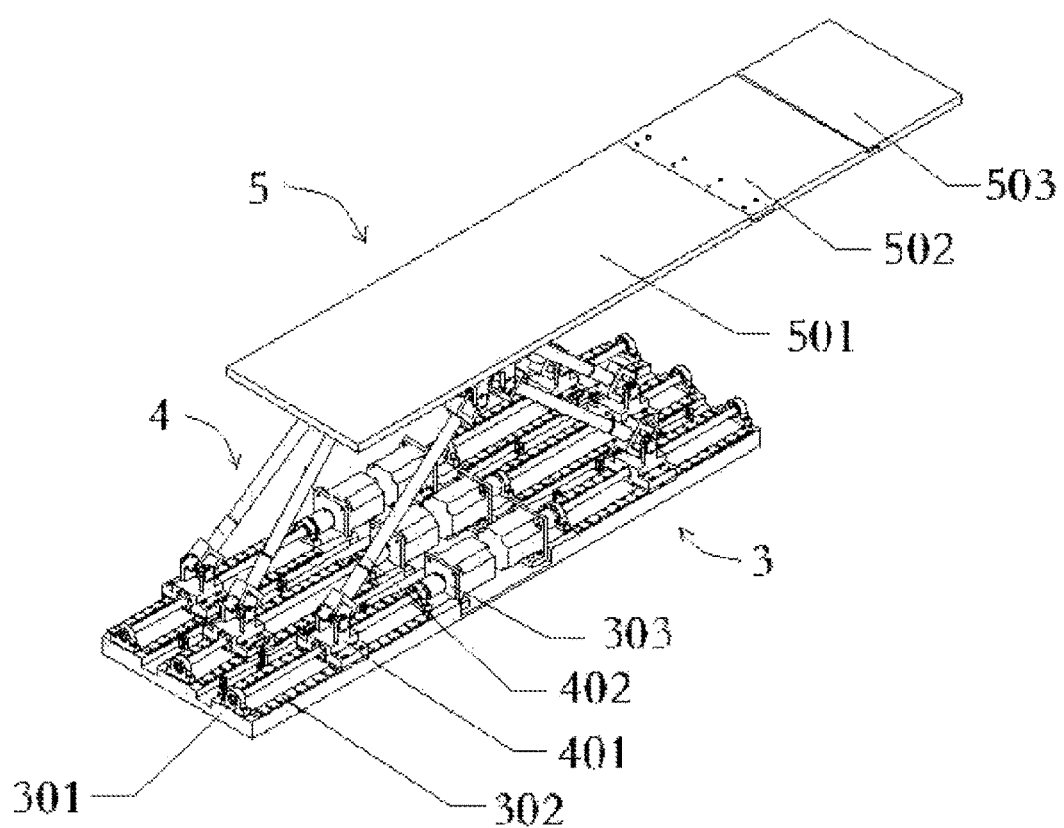
FIG. 7 is a schematic diagram of a six-degree-of-freedom parallel radiation therapy bed in the radiation therapy system of the present invention.
Figure 8:
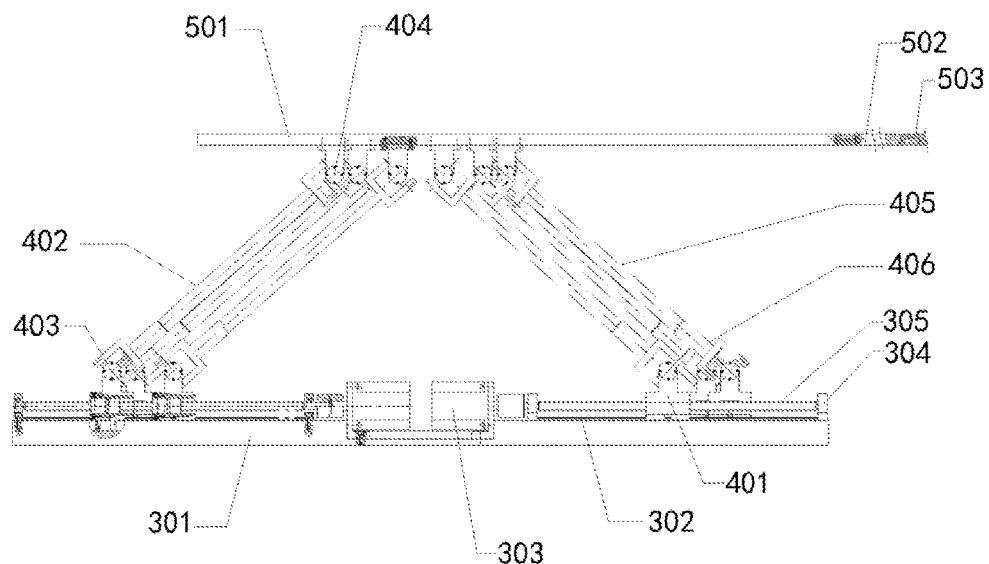
FIG. 8 is a side view of the six-degree-of-freedom parallel radiation therapy bed in the radiation therapy system of the present invention.
Figure 9:
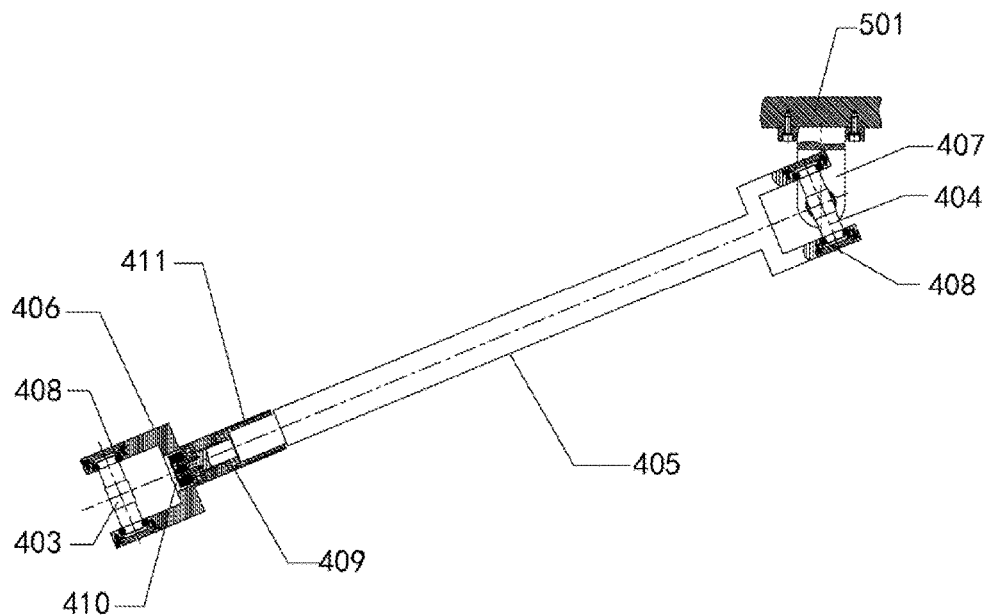
FIG. 9 is a schematic diagram of a connecting rod assembly in the radiation therapy system of the present invention.
Figure 10:
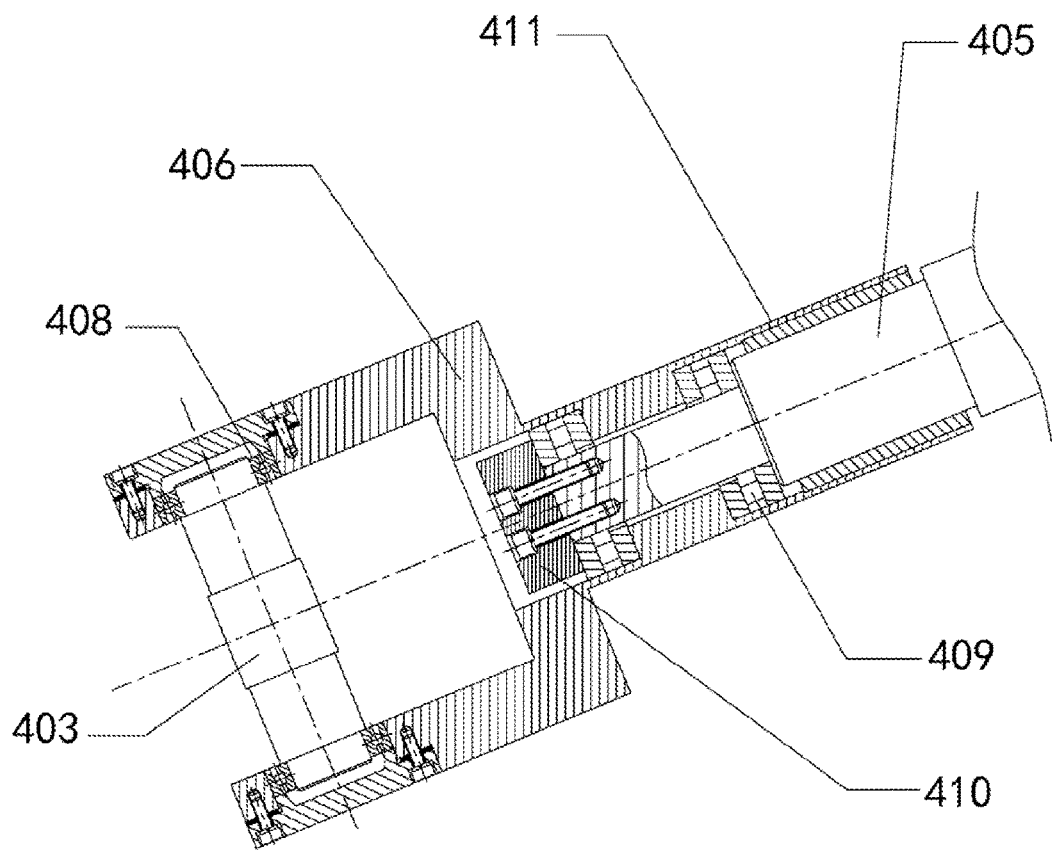
FIG. 10 is a schematic diagram of a joint of an upper connecting rod and a lower connecting rod in the radiation therapy system of the present invention.
Figure 11:
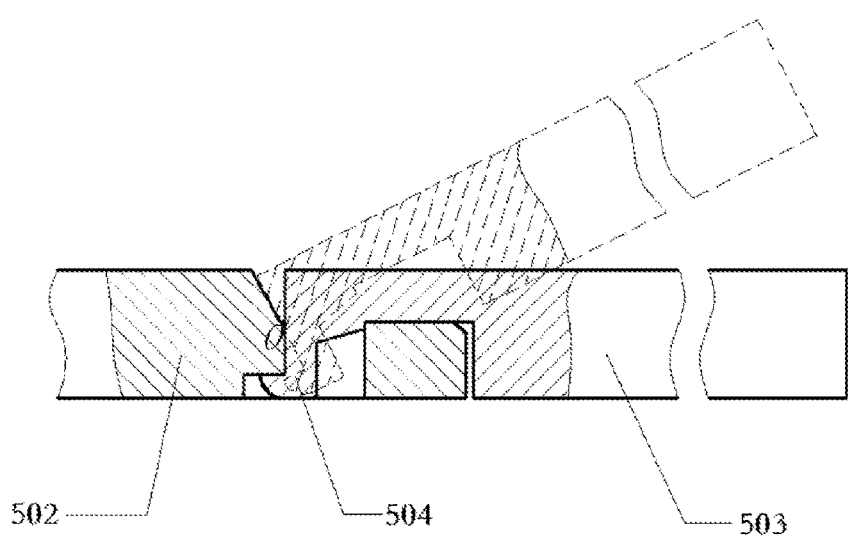
FIG. 11 is a schematic diagram of a joint of a middle bed plate and an additional bed plate in the radiation therapy system of the present invention.

Referring to FIGS. 7 to 11, the six-degree-of-freedom parallel radiation therapy bed in the radiation therapy system of the present invention includes a base assembly 3, a connecting rod assembly 4 and a bed plate assembly 5. The base assembly 3 includes a base 301, a plurality of sliding rails 302 disposed on the base side by side and a power unit 303 fixed on the base. The connecting rod assembly 4 includes a sliding base 401 and a connecting rod 402, the sliding base 401 is driven by the power unit 303 to relatively slide on the sliding rail 302, and the bottom end of the connecting rod 402 is rotatably connected with the sliding base 401. The bed plate assembly 5 includes a main bed plate 501, and the top end of the connecting rod 402 is rotatably connected with the main bed plate 501. In order to achieve the six-degree-of-freedom and multi-position flexible adjustment, there are six sliding rails 302, where three sliding rails 302 are parallelly disposed on the top surface of the front side of the base 301, and the other three sliding rails 302 are parallelly disposed on the top surface of the rear side of the base, there are six connecting rod assemblies 4, and the sliding bases 401 of the six connecting rod assemblies 4 relatively slide on the respective sliding rails 302.

It should be noted that, there are various embodiments of the base assembly, and all the base assemblies which are capable of driving the sliding base to relatively slide on the sliding rail should fall within the scope of protection of the present invention. For example, the power unit is provided as a cylinder or a hydraulic cylinder and the output end of the cylinder or the hydraulic cylinder is connected with the sliding base. In order to control stability and accuracy, in the radiation therapy system of the present invention, the base assembly 3 further includes bearing supports 304 disposed on the top surfaces of the front and rear sides of the base 301 and lead screws 305 disposed parallel to the sliding rails 302, the sliding rails 302 and the bearing support 304 are mounted on a lug boss of the top surface of the base 301, the power unit 303 is disposed on the middle portion of the top surface of the base 301 and located between ends of the sliding rails 302, one end of the lead screw 305 is disposed on the bearing support by a bearing, the other end of the lead screw 305 is in driving connection with the power unit 303, and the power unit is simply provided as a servo motor. A nut sleeve (not shown) is disposed at the bottom of the sliding base 401, the nut sleeve rotates relative to the lead screw 305, the servo motors are controlled by a computer system to rotate in a forward or reverse direction so as to control the rotation of the lead screw and thus the lifting movement of the connecting rod.

In order to achieve free rotation of the connecting rod between the slide base and the main bed plate, in the radiation therapy system of the present invention, the bottom of the connecting rod 402 is rotatably connected with the sliding base 401 by a first cross shaft 403 and the top of the connecting rod 402 is rotatably connected with a hooke joint 407 at the bottom of the main bed plate 501 by a second cross shaft 404. In addition, bearings 408 are disposed respectively between the first cross shaft 403 and the bottom of the connecting rod 402, between the first cross shaft 403 and the sliding base 401, between the second cross shaft 404 and the top of the connecting rod 402, and between the second cross shaft 404 and the hooke joint at the bottom of the main bed plate 501.

In the radiation therapy system of the present invention, the connecting rod 402 includes an upper connecting rod 405 and a lower connecting rod 406, a thrust bearing 409 is disposed between the top end of the lower connecting rod 406 and the bottom end of the upper connecting rod 405, and an end cap 410 is further disposed on the bottom end of the lower connecting rod 406 for limiting the relative position of the upper connecting rod 405 and the lower connecting rod 406, and a copper sleeve 411 cooperating with the bottom of the upper connecting rod 405 is further disposed on the outer side of the top end of the lower connecting rod 406. Circumferential positioning of the upper connecting rod is achieved by the copper sleeve, axial positioning of the upper connecting rod is achieved by the thrust bearing, and fastening of the upper connecting rod and the lower connecting rod is achieved by the end cap.

In the radiation therapy system of the present invention, the bed plate assembly 5 further includes a middle bed plate 502 and an additional bed plate 503. The middle bed plate is fixedly connected with the main bed plate, and the additional bed plate is fixed at the end of the middle bed plate by a suspension fixture. The main bed plate is a metal main bed plate, and the middle bed plate is a carbon fiber middle bed plate. When a therapy head performs radiation therapy, a metal material between the therapy head and the receivers below the therapy head is not allowed since the metal material may influence imaging within the receivers, and thus the bed plate is designed with a three-segment structure in order to save the carbon fiber material. The main bed plate is of a metal material, the middle bed plate is of a carbon fiber material, and the first two segments of bed plates are connected together by bolts, and when the head is treated, only the two segments of bed plates are needed. When the thorax and abdomen need to be treated, the additional bed plate is mounted, and since a metal material is not allowed, both bed plates are connected by means of snap joint, and mounting and detaching can be accomplished by rotation at a certain angle.

The working process of the present invention is: 1) data collection and modeling: the O-shaped arm and the radiation therapy bed are adjusted, and multi-modal images are collected through X-rays of the double-X-ray machine image positioning mechanism on the O-shaped arm; a mathematical model is established; physical dose parameters of the radiation therapy system are collected with definitions and scales of a positioned coordinate system; 2) pretreatment prior to radiation therapy: multi-modal image registration is performed on the multi-modal images and the mathematical model, and a model and three-dimensional dynamic display is established by combining with the coordinate system, then a radiotherapy regimen is designed and formulated in combination with the physical dose parameters of the radiation therapy system, and the whole treatment process is dynamically simulated according to the radiotherapy regimen and the three-dimensional dynamic display; and 3) treatment during radiation therapy: positioning and registration of a three-dimensional image of a target region during the therapy is obtained by adjusting the O-shaped arm in combination with the model and the three-dimensional dynamic display and a result of real-time dose verification, intervention and correction is performed during the treatment process, and corrections are returned to the step of designing and formulating the radiotherapy regimen; then the intervention and correction during the treatment process and the dynamical simulation of the whole treatment process are controlled commonly for automatic tracking and positioning of the irradiation.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A radiation therapy system, comprising: a five-degree-of-freedom O-shaped arm radiation therapy device and a six-degree-of-freedom parallel radiation therapy bed, wherein
   the five-degree-of-freedom O-shaped arm radiation therapy device comprises an O-shaped arm movement mechanism, a linear accelerator device, a radiation dose detection device, and a double-X-ray machine image positioning mechanism,
   the O-shaped arm movement mechanism comprises:
      an O-shaped arm;
      an accelerator displacement device for driving the linear accelerator device to displace relatively towards a central position of the O-shaped arm;
      a horizontal longitudinal displacement device comprising a first slide rail and a first slide base disposed at both sides of the O-shaped arm, and a first power unit for driving the first slide base to relatively slide on the first slide rail, two sets of the first slide rails and the first slide bases being provided;
      a horizontal transverse displacement device comprising a second slide rail and a second slide base disposed on the first slide base, and a second power unit for driving the second slide base to relatively slide on the second slide rail, two sets of the second slide rails and the second slide bases being provided, and the slide directions of the second slide bases and the first slide bases being vertical to each other;
      a turning displacement device comprising a third power unit disposed on the second slide bases; and
      a rotational displacement device comprising a turning seat disposed at an output end of the third power unit and a fourth power unit, the third power unit being used for turning the rotational displacement device, and a turning plane of the rotational displacement device being vertical to a slide direction of the second slide bases, the O-shaped arm being disposed between two sets of turning seats, and the fourth power unit being used for driving the O-shaped arm to relatively displace on the turning seats;
      the linear accelerator device is mounted on the O-shaped arm by the accelerator displacement device;
      the radiation dose detection device is disposed on the O-shaped arm at a side opposite to the linear accelerator device;
      the double-X-ray machine image positioning mechanism comprises an X-ray transmitter disposed on the O-shaped arm and an X-ray receiver disposed on the O-shaped arm at a side opposite to the X-ray transmitter, two sets of the X-ray transmitters and the X-ray receivers being provided; and
      the six-degree-of-freedom parallel radiation therapy bed comprises:
         a base assembly comprising a base, a plurality of sliding rails disposed on the base side by side, and a power unit fixed to the base;
         a connecting rod assembly comprising a sliding base which is driven by the power unit to relatively slide on the sliding rails and a connecting rod, a bottom end of the connecting rod being rotatably connected with the sliding base; and
         a bed plate assembly comprising a main bed plate, a top end of the connecting rod being rotatably connected with the main bed plate.

2. The radiation therapy system as claimed in claim 1, wherein a plurality of annular slide grooves are disposed on a side surface of the O-shaped arm, limiting plates being fixed at both sides of front and rear ends of the turning seats, and slide blocks engaged and relatively sliding in the slide grooves being disposed at the inner side of the limiting plates.

3. The radiation therapy system as claimed in claim 1, wherein
   the first power unit comprises:
   a first servo motor;
   a first lead screw disposed at an output end of the first servo motor and parallel to the first slide rails; and
   a first lead screw sleeve fixed at the bottom of the first slide bases and relatively rotatable on the first lead screw; and
   the second power unit comprises:
   a second servo motor;
   a second lead screw disposed at an output end of the second servo motor and parallel to the second slide rail; and
   a second lead screw sleeve fixed at the bottom of the second slide bases and relatively rotatable on the second lead screw.

4. The radiation therapy system as claimed in claim 1, wherein the third power unit comprises a third servo motor fixed to the second slide bases, the turning seats being fixed at an output end of the third servo motor.

5. The radiation therapy system as claimed in claim 1, wherein the fourth power unit comprises a fourth servo motor fixed to the turning seats and a driving gear disposed at an output end of the fourth servo motor, a synchronous belt being disposed on the outer side surface of the O-shaped arm, and the fourth servo motor driving relative displacement of the O-shaped arm on the turning seats through interaction of the driving gear and the synchronous belt.

6. The radiation therapy system as claimed in claim 1, wherein the accelerator displacement device comprises:
   a base plate fixed to the O-shaped arm;
   a fifth servo motor fixed to the base plate;
   a plurality of third lead screws vertically fixed to the bottom of the base plate; and a plurality of third lead screw sleeves fixed to the linear accelerator device and relatively rotatable on the third lead screws.

7. The radiation therapy system as claimed in claim 1, wherein there are six sliding rails, three sliding rails being parallelly disposed on the top surface of the front side of the base and the other three sliding rails being parallelly disposed on the top surface of the rear side of the base;

there are six connecting rod assemblies, sliding bases of the six connecting rod assemblies relatively sliding on the respective sliding rails;

the base assembly further comprises bearing supports disposed on the top surfaces of the front and rear sides of the base and lead screws disposed parallel to the sliding rails, the power unit being disposed at the middle part of the top surface of the base and located between ends of the sliding rails, one end of the lead screws being disposed on the corresponding bearing support by the corresponding bearing, the other end of the lead screws being in driving connection with the power unit;

a nut sleeve being disposed at the bottom of the sliding bases and rotatable relative to the corresponding lead screw.

8. The radiation therapy system as claimed in claim 1, wherein the sliding base is rotatably connected to the bottom of the connecting rod by a first cross shaft, and a hooke joint at the bottom of the main bed plate is rotatably connected to the top of the connecting rod by a second cross shaft.

9. The radiation therapy system as claimed in claim 1, wherein the connecting rod comprises an upper connecting rod and a lower connecting rod, a thrust bearing being disposed between a top end of the lower connecting rod and a bottom end of the upper connecting rod, and an end cap being provided on a bottom end of the lower connecting rod for limiting a relative position of the upper connecting rod and the lower connecting rod, and a copper sleeve cooperating with the bottom of the upper connecting rod being further disposed on the outer side of the top end of the lower connecting rod.

10. The radiation therapy system as claimed in claim 1, wherein the bed plate assembly further comprises:

a middle bed plate fixedly connected with the main bed plate; and an additional bed plate fixed at an end of the middle bed plate by a suspension fixture;

wherein the main bed plate is a metal main bed plate, and the middle bed plate is a carbon fiber middle bed plate.

* * * * *